United States Patent [19]

Obayashi et al.

[11] 4,210,509

[45] Jul. 1, 1980

[54] OXYGEN SENSOR

[75] Inventors: Hidehito Obayashi, Tokyo; Hiroshi Okamoto, Ohme, both of Japan

[73] Assignee: Hitachi, Ltd., Tokyo, Japan

[21] Appl. No.: 936,129

[22] Filed: Aug. 23, 1978

[30] Foreign Application Priority Data

Sep. 2, 1977 [JP] Japan ................................. 52-104966

[51] Int. Cl.² ............................................. G01N 27/58
[52] U.S. Cl. ................................. 204/195 S; 106/73.1
[58] Field of Search .............. 204/195 S, 1 S; 324/29;
123/119 E, 119 EC; 106/73.1; 429/193

[56] References Cited

U.S. PATENT DOCUMENTS

| | | | |
|---|---|---|---|
| 3,698,955 | 10/1972 | Lilly et al. ..................... | 204/195 S X |
| 3,699,032 | 10/1972 | Rapp ................. | 204/195 S |
| 3,719,564 | 3/1973 | Lilly et al. ..................... | 204/195 S X |

FOREIGN PATENT DOCUMENTS 48-90294  2/1973 Japan .
49-126390 12/1974 Japan .
50-137591 10/1975 Japan .

OTHER PUBLICATIONS

Eckehardt Hamann et al., Soc. Automotive Engineers, Paper No. 770401, Feb. 1977.
Heinrich Dueker et al., Soc. Automotive Engineers, Paper No. 750,223, Feb. 1975.
William Fleming, Res. Labs., General Motors Corp., Pub. GMR-2128, Apr. 1976.
William Fleming, Res. Labs., General Motors Corp., Pub. GMR-1971R, Sep. 1975.
A. L. Cederquist et al., Soc. Automotive Engineers, Paper No. 760202 (No date).

*Primary Examiner*—G. L. Kaplan
*Attorney, Agent, or Firm*—Craig & Antonelli

[57] ABSTRACT

An oxygen sensor comprising an oxygen ion conductive solid electrolyte which contains fluorine at least in the surface region on the side having contact with a gas to be tested. This oxygen sensor is characterized in that the change of the electromotive force at an $O_2/CO$ molar ratio of about 0.5:1 is very large even if the temperature is as low as 350° C.

6 Claims, 8 Drawing Figures

OXYGEN SENSOR

BACKGROUND OF THE INVENTION (1) Field of the Invention

The present invention relates to an oxygen sensor. More particularly, the invention relates to an oxygen sensor comprising an oxygen ion conductive solid electrolyte.

(2) Description of the Prior Art

Various oxygen sensors for determining oxygen concentrations in various gases are known in the art. For determination of the oxygen concentration in high temperature gases, an oxygen sensor comprising an oxygen ion conductive solid electrolyte is used most broadly.

As shown in FIG. 1, this oxygen sensor comprises an oxygen ion conductive solid electrolyte 1 molded to have an optional shape and voltage pick-up electrodes 2 and 3 coated on the two main surfaces of the molded solid electrolyte 1, respectively. When one electrode is exposed to an appropriate standard gas (for example, air), if the other electrode is caused to fall in contact with a gas containing free oxygen, oxygen in the gas is converted to an oxygen ion by electrochemical oxidation-reduction reaction. Accordingly, a voltage is generated between both the electrodes, and this voltage corresponds to the concentration of oxygen in the gas.

When two gases 4 and 5 differing in the oxygen concentration are caused to fall in contact with both the surfaces of the oxygen ion conductive solid electrolyte 1, a concentration cell is formed, and a voltage corresponding to the difference of the oxygen concentration is generated between both the electrodes 2 and 3. Accordingly, when a standard gas having a known concentration (in general, air is used) is caused to fall in contact with one surface of the oxygen conductive solid electrolyte and a gas to be tested is caused to fall in contact with the other surface, the oxygen concentration in the gas to be tested can be determined from the voltage generated between the two electrodes.

As the oxygen ion conductive solid electrolyte for an oxygen sensor, solid solutions of $ZrO_2$, $HfO_2$, $CeO_2$ or $ThO_2$ with at least one member selected from MgO, CaO, and rare earth element oxides such as $Y_2O_3$ and $Nd_2O_3$ can be used. So-called "stabilized zirconia" such as $ZrO_2$—$Y_2O_3$ or $ZrO_2$—CaO is most popularly used as the oxygen ion conductive solid electrolyte. However, oxygen sensors comprising these oxygen ion conductive solid electrolytes are defective in that when they are used at lower temperatures below 500° C., the overvoltage of the electrode reaction becomes extreme and no good characteristics can be obtained, though they show excellent characteristics at higher temperatures, for example, about 1000° C.

Accordingly, when such conventional oxygen sensor is used for determining the oxygen concentration in, for example, an automobile exhaust gas, good results can be obtained if an automobile is driven at a high speed and the temperature of the exhaust gas is high, but if the driving speed is low and the temperature of the exhaust gas is lowered, no good results can be obtained. Because of such inferior low temperature characteristics, the application range of conventional oxygen sensors of this type is drastically restricted.

Various attempts have heretofore been made to improve such inferior low temperature characteristics. For example, contrivances have been made on the method of forming electrodes of a noble metal, and there has been proposed a method in which a special oxide is used as an electrode-constituting material. However, no satisfactory results can be obtained according to these proposals.

List of the Prior Art [37CFR1.56(a)]

The following references are cited to show the state of the art:

(1) Japanese Patent Application Laid-Open Specification No. 137591/1975

(2) Japanese Patent Application Laid-Open Specification No. 90294/1973

(3) Japanese Patent Application Laid-Open Specification No. 126390/1974

(4) SAE Paper 770401 (Feb. 28, 1977, Detroit), "Lambda Sensor with $Y_2O_3$ Stabilized Zirconia Ceramic"

(5) SAE Paper 750223, "Ceramic Aspect of the Bosch Lambda Sensor"

(6) GM Res. Publication GMR-2128 (Apr. 12, 1976)

(7) GM Res. Publication GMR-1971R (Sept. 11, 1975)

(8) SAE Paper 760202, "Characterization of Zirconia and Titania Engine Exhaust Gas Sensors"

The foregoing references disclose oxygen sensors formed by using various oxygen ion conductive solid electrolytes such as $ZrO_2$—$Y_2O_3$, but improvements of characteristics by incorporation of fluorine are not taught in any of these references.

SUMMARY OF THE INVENTION

It is a primary object of the present invention to solve the foregoing problems involved in the conventional oxygen sensors and provide an oxygen sensor showing good characteristics not only at high temperatures but also at lower temperatures.

This and other objects of the present invention can be attained by an oxygen sensor comprising an oxygen ion conductive solid electrolyte containing fluorine at least in the vicinity of the surface with which a gas to be tested is caused to fall in contact and electrodes formed on both the main surfaces of said oxygen ion conductive solid electrolyte, respectively.

DETAILED DESCRIPTION OF THE PREFERRED EMBODIMENTS

Figure 1:
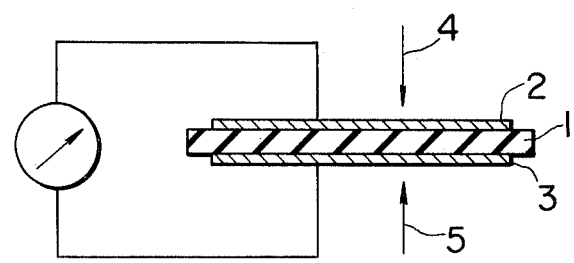
FIG. 1 is a diagram illustrating the functions of an oxygen sensor comprising an oxygen ion conductive solid electrolyte.

As pointed out hereinbefore, in the oxygen sensor of the present invention, the oxygen ion conductive solid electrolyte contains fluorine at least in the vicinity of the surface with which a gas to be tested is caused to fall in contact. Fluorine may be contained not only on the side to be contacted with a gas to be tested but also in the vicinity of the surface on the side to be contacted with a standard gas or in other parts. Further, in the present invention, fluorine may be incorporated even in the central portion of the oxygen ion conductive solid electrolyte from the surface region thereof.

Such fluorine-containing oxygen ion conductive solid electrolyte that is used in the present invention can be formed according to the following three methods.

1. An oxygen ion conductive solid electrolyte is molded into a desirable shape and sintered, and the sintered solid electrolyte is treated with a solution containing a fluorine ion or fluorine. As the solution, there can be used, for example, an aqueous solution of hydrofluoric acid, an aqueous solution of ammonium fluoride, an aqueous solution of sodium fluoride and fluorine-containing organic solvents. According to this method, fluorine can be incorporated in the surface region of the solid electrolyte.

2. An oxygen ion conductive solid electrolyte is molded into a desirable shape and sintered, and the sintered electrolyte is placed in fluorine vapor or fluorine-containing vapor. According to this method, fluorine can be incorporated in the surface region of the solid electrolyte. For example, when the oxygen ion conductive solid electrolyte and yttrium fluoride ($YF_3$) are placed in one vessel and they are maintained at a predetermined temperature, fluorine vapor is generated and is included in the surface region of the oxygen ion conductive solid electrolyte. This method can be conducted in the closed system, and when the pressure of fluorine vapor is sufficiently high, the chemical vapor deposition (CVD) method may be adopted. In addition, the sputtering deposition method may be adopted.

3. A fluorine compound is incorporated in the starting material and an oxygen ion conductive solid electrolyte is prepared therefrom. In this case, fluorine can be incorporated not only in the surface region but also throughout the entire structure. For example, in case of a solid electrolyte of the $Y_2O_3$ type, if a part of $Y_2O_3$ is substituted with $YF_3$ and sintering are then conducted, there can be obtained a solid electrolyte of the $ZrO_2$—$Y_2O_3$ type in which fluorine is distributed substantially uniformly.

The present invention will now be described in detail by reference to the following Examples that by no means limit the scope of the invention.

EXAMPLE 1

A disc-like sintered body of stabilized zirconia having a $ZrO_2$:$Y_2O_3$ molar ratio of 92:8, which was 1 to 2 mm in thickness and about 20 mm in diameter and had a sintering degree of about 95%, was dipped in a 10% aqueous solution of HF for 30 minutes and then washed in running water for 30 minutes.

On each of both the surfaces of the sintered body, a platinum electrode was coated in a circular region having a diameter of about 12 mm and baked, and there was assembled an oxygen sensor of the concentration cell type having a structure of $H_2$ (or CO)+$O_2$, Pt/$ZrO_2$—$Y_2O_3$/Pt, air. Characteristics of the sensor at 350° C. were examined. For comparison, an oxygen sensor was prepared in the same manner as described above except that the sintered body was not treated with the aqueous solution of HF, and characteristics of this sensor at 350° C. were similarly examined.

Figure 2:
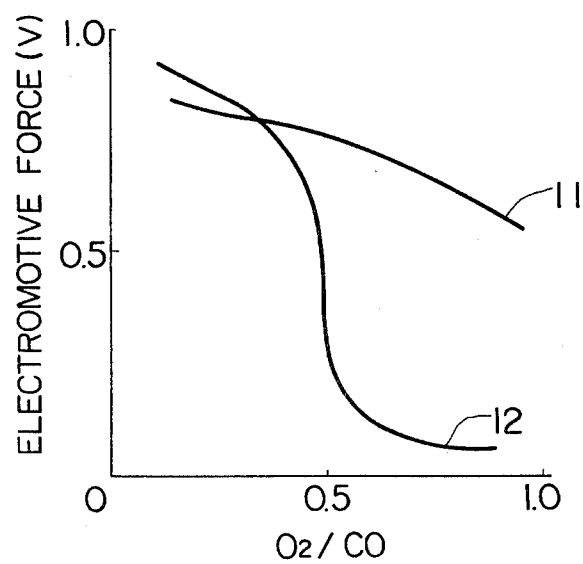
FIG. 2 shows a curve comparing characteristics of a solid electrolyte treated with an aqueous solution of HF with characteristics of an untreated solid electrolyte.

Obtained results are shown in FIG. 2. Curve 12 shows characteristics of the oxygen sensor of the present invention in which the treatment with the aqueous solution of HF was carried out, and curve 11 shows characteristics of the comparative oxygen sensor in which the treatment with the aqueous solution of HF was not carried out.

As will be apparent from the results shown in FIG. 2, the electromotive force of the oxygen sensor treated with the aqueous solution of HF shows good rising when the $O_2$:CO molar ratio is about 1:2 (the residual oxygen is substantially zero), and the electromotive force characteristic corresponds substantially to the theoretical characteristic.

As seen from curve 11, in the oxygen sensor not treated with the aqueous solution of HF, the change of the electromotive force with the change of the oxygen concentration is very small.

As a means for preventing air pollution by automobile exhaust gases, there has been proposed a method in which the oxygen concentration in an automobile exhaust gas is measured and the amount of air mixed into a fuel is adjusted according to the obtained result so that air is introduced into an engine exactly in an amount necessary for complete combustion of the fuel. An oxygen sensor that is used for working such method is required to show a highest sensitivety where the amount of oxygen mixed in a fuel is substantially equal to the amount of oxygen just necessary for complete combustion of the fuel.

Namely, as will be apparent from the reaction formula of $CO + \frac{1}{2}O_2 \rightarrow CO_2$, the amount of oxygen just necessary for complete combustion of 1 mole of CO is 0.5 mole, and therefore, in order to incorporate oxygen precisely in an amount necessary for complete combustion, the oxygen sensor should act most sensitively when the CO:$O_2$ molar ratio is about 1:0.5.

From the results shown in FIG. 2, it will readily be understood that the oxygen sensor of the present invention can be used for this purpose more conveniently than the conventional oxygen sensors.

In order to know the state of distribution of fluorine in the above-mentioned sintered body treated with the aqueous solution of HF, the test was carried out by using an ion micro analyzer (IMA). Accordig to the IMA measurement, exactly quantitative results cannot be obtained, but relative quantities of fluorine present can be determined. Namely, if the measurement is repeated at one point, the distribution of fluorine with respect to the direction of the depth at this point can be known.

Figure 3:
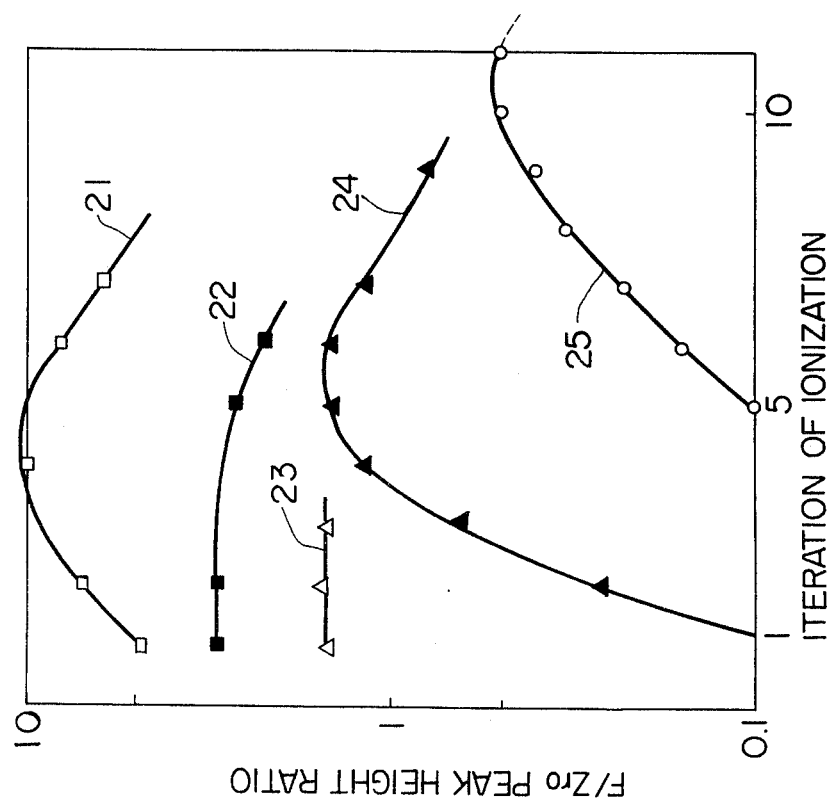
FIG. 3 is a diagram illustrating the state of distribution of fluorine in the surface region of a solid electrolyte.

FIG. 3 shows results of the IMA measurement. Namely, curves 21, 22, 23, 24 and 25 show results obtained when the measurement was carried out repeatedly at 5 different points. Since the IMA measurement lacks the quantitativeness as pointed above, the peak ratio of fluorine and zirconium as the main component is plotted on the ordinate and the iteration of ionization (the frequency of repeatition of the measurement) is plotted on the abscissa.

The oxygen ion conductive solid electrolyte used as the sample was a polycrystalline sintered body which was relatively porous. Since the IMA measurement is for analysis in a microfine region of several $\mu m^2$, the obtained F/Zr intensity ratio differed according to the measurement points, but it was found that at each measuring point, fluorine was contained in the surface region of the sintered body and the F/Zr intensity ratio was in the range of from about 0.5 to about 10.

Then, the above-mentioned sintered body was gradually polished from the surface, and the relation between the polished thickness (the depth from the surface) and the F/Zr intensity ratio was determined to obtain results shown in Table 1.

Table 1

| Depth ($\mu m$) from Surface | F/Zr Intensity Ratio |
| --- | --- |
| 0 | 0.5–10 |
| 50 | 0.05–0.1 |
| 100 | 0.001 |
| 150 | ≃0 |
| 200 | ≃0 |

As will be apparent from the data shown in Table 1, by the above-mentioned treatment with the aqueous solution of HF, fluorine was included in the region of a depth of about 50 $\mu m$ from the surface in the above-mentioned sintered body. Accordingly, it will readily be understood that if fluorine is contained in the surface region, there can be obtained an oxygen sensor having preferred characteristics. It will also be understood that the amount of fluorine present in the surface (a depth of ~0 $\mu m$) is much larger than the amount of fluorine present in other portions. Thus, it will readily be understood that fluorine present in the surface region makes contributions to improvements of the characteristics in the oxygen sensor and if fluorine is present at least in the surface region, there can be obtained an oxygen sensor having excellent characteristics.

In this Example, the aqueous solution of HF was used for the treatment of an oxygen ion conductive solid electrolyte. By experiments conducted separately, it has been confirmed that similar results can be obtained when acidic solutions of NaF and $NH_4F$ and fluorine-containing organic solvents are used instead of an aqueous solution of HF.

EXAMPLE 2

In this Example, a fluorine compound was added to the starting substance, and an oxygen ion conductive solid electrolyte was prepared, molded and sintered to form a sintered body in which fluorine was distributed substantially uniformly.

$ZrO_2$, $Y_2O_3$ and $YF_3$ were mixed at a molar ratio of 92:8:0–10 and the mixture was pulverized and calcined at 1,400° C. The calcined product was sufficiently pulverized and compression-molded to obtain a disc similar to that obtained in Example 1. Then, the disc was heated at 1,600° C. to form a disc-like sintered body.

In the same manner as described in Example 1, an oxygen sensor was prepared by using the so obtained sintered body, and the characteristics of the oxygen sensor were examined. Obtained results are shown in FIG. 4.

Figure 4:
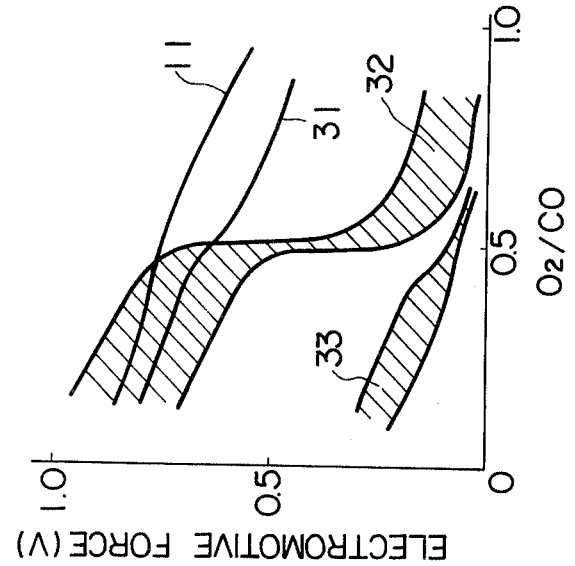
FIG. 4 is a curve illustrating the relation between the fluorine content and characteristics of a solid electrolyte.

In FIG. 4, curve 11 shows characteristics observed when $YF_3$ was not added and curve 31 shows characteristics obtained when the amount added of $YF_3$ was 0.0005 mole, and hatched regions 32 and 33 show characteristics obtained when the amount added of $YF_3$ was in the range of 0.001 to 0.02 mole and in the range of 0.03 to 10 moles, respectively.

As will readily be understood from the results shown in FIG. 4, when the amount added of $YF_3$ is 0.001 to 0.02 mole, a highest sensitivity to the change of the oxygen concentration can be obtained at an $O_2/CO_2$ molar ratio of about 0.5. When the amount of $YF_3$ added is 0.0005 mole or zero, the change of the electromotive force with the change of the oxygen concentration is very small and such oxygen sensor cannot be put into practical use. When the amount of $YF_3$ added is too large, for example, 0.03 mole or larger, the characteristics are drastically degraded and an oxygen sensor that can be put into practical use cannot be obtained. The reason why the characteristics are degraded if the amount of $YF_3$ added is 0.03 mole or larger is construed to be that the ionic conductivity of the solid electrolyte is reduced. Further, if the amount of $YF_3$ added is too large, the sintering property is reduced, resulting in degradation of the mechanical strength. Accordingly, it is preferred that the amount of $YF_3$ added be 0.001 to 0.02 mole (0.04 ~ 0.8 w/o as fluorine wherein w/o represents weight %).

EXAMPLE 3

In this Example, a molded and sintered oxygen ion conductive solid electrolyte was treated in an atmosphere containing fluorine vapor to incorporate fluorine in the surface region of the solid electrolyte.

Figure 5:
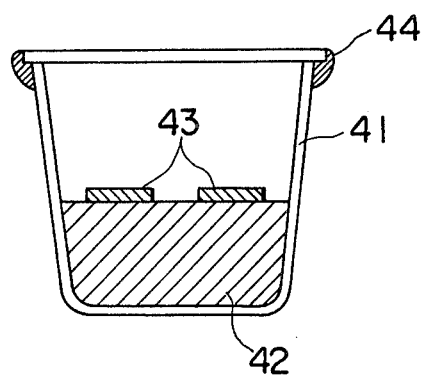
FIG. 5 is a diagram illustrating a method for incorporating fluorine in the surface region of a solid electrolyte by using fluorine vapor.

As shown in FIG. 5, $YF_3$ powder 42 and a molded and sintered plate-like oxygen ion conductive solid electrolyte 43 were charged in an alumina crucible 41 having a lid, and the crucible 41 was sealed with an alumina cement 44 so that the atmosphere in the crucible 41 could be maintained. Then, the crucible 41 was placed in an electric furnace and the heat treatment was carried out at 1,000° to 1,400° C. for 1 to 2 hours.

By the above heat treatment, a part of $YF_3$ was evaporated and fluorine was permeated into the solid electrolyte 43 from the surface thereof, and therefore, fluorine was incorporated in the surface region of the solid electrolyte.

In the same manner as described in Example 1, electrodes were formed on both the surfaces of the so treated oxygen ion conductive solid electrolyte to form an oxygen sensor. When the characteristics of the oxygen sensor were determined, it was found that the characteristics were included in the region 32 in FIG. 4. Thus, it was confirmed that this oxygen sensor could be put into practical use sufficiently.

EXAMPLE 4

As illustrated in Example 1, the HF treatment of the surface of an oxygen ion conductive solid electrolyte is very effective for improving the characteristics. In this Example, the influences of the HF concentration at the HF treatment on the characteristics of the oxygen sensor were examined to obtain results shown in FIG. 6.

Figure 6:
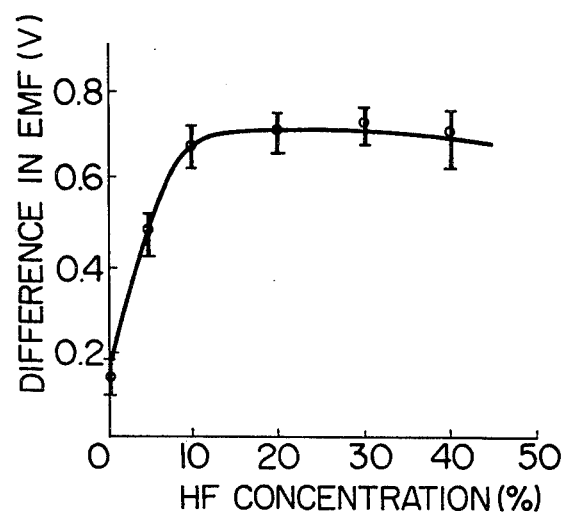
FIG. 6 is a curve illustrating the relation between the concentration of an aqueous solution of HF and the electromotive force characteristic.

In FIG. 6, the ordinate indicates the difference of the electromotive force as measured at 350° C. between the case where the $O_2/CO$ molar ratio was 0.2 and the case where the $O_2/CO$ molar ratio was 0.8.

As is apparent from the results shown in FIG. 6, the difference of the electromotive force is increased with increase of the HF concentration, and when the treatment is conducted at an HF concentration of at least 5%, an oxygen sensor that can be put into practical use can be formed.

A protecting film (magnesium spinel film) was attached to this oxygen sensor element, and the assembly was attached to the vicinity of a manifold of an exhaust gas pipe of a bench engine and the characteristics of the oxygen sensor element were tested while an actual exhaust gas was contacted with the element. As a result, it was confirmed that this oxygen sensor element according to the present invention has a sensitivity sufficient to determine the oxygen concentration in an actual automobile exhaust gas.

In this Example, the HF treatment was conducted for 30 minutes. It was found that when the HF concentration was higher than 30%, leaching of the solid electrolyte with HF became conspicuous and degradation of the characteristics was caused to such an extent that the resulting oxygen sensor could not be put into practical use. Accordingly, from the practical viewpoint, it is preferred that the HF concentration be in the range of from about 5 to about 30%.

EXAMPLE 5

Figure 7:
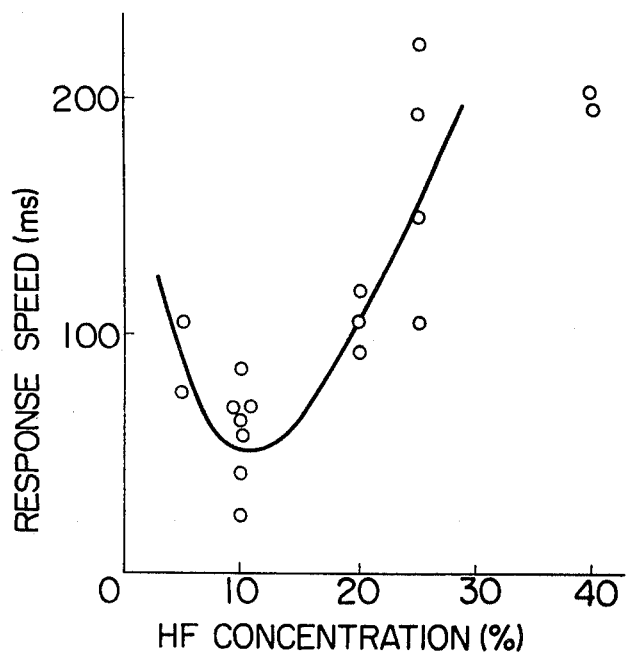
FIG. 7 is a curve illustrating the relation between the concentration of an aqueous solution of HF and the response speed characteristic.

In this Example, the relation between the concentration of an aqueous solution of HF used for the treatment of an oxygen ion conductive electrolyte and the response speed of the resulting oxygen sensor was examined to obtain results shown in FIG. 7.

In FIG. 7, the ordinate indicates the response speed. The experiment was carried out on an exhaust gas (maintained at 400° C.) from the bench engine as used in Example 4. The air-fuel ratio was instantaneously changed from 14 to 17, and the time required for the electromotive force of the oxygen sensor element to be reduced to 0.3 V from 0.6 V was measured and the response speed was expressed in terms of the so measured time.

From the practical viewpoint, it is preferred that this response speed be less than about 100 milliseconds. It was found that if an oxygen ion conductive solid electrolyte is treated with an aqueous solution of HF having a concentration of about 5 to about 20%, the response speed is less than about 100 milliseconds.

EXAMPLE 6

An oxygen ion conductive solid electrolyte molded and sintered in the same manner as described in Example 1 was used as a sample, and this sample was treated with an aqueous solution of HF under conditions indicated in Table 2 and then heat-treated under conditions indicated in Table 2. The concentration of fluorine left in the surface region was determined according to the IMA method in the same manner as described in Example 1. By using the so treated sample, an oxygen sensor was assembled and the difference of the electromotive force (350° C.) between the case of the $O_2/CO$ molar ratio of 0.2 and the case of the $O_2/CO$ molar ratio of 0.8 was determined. Obtained results are shown in Table and FIG. 8.

Table 2

| Sample No. | HF Treatment | Water Washing | Heat Treatment | Concentration of F Left in Surface (F/Zr) |
|---|---|---|---|---|
| 1 | not conducted | not conducted | not conducted | $6 \times 10^{-4}$ |
| 2 | 10% HF, 30 minutes | 30 minutes in running water | 800° C., 1 hour, in air | $10\text{-}4 \times 10^{-1}$ |
| 3 | 10% HF, 30 minutes | 30 minutes in running water | 950° C., 1 hour, in air | $10\text{-}2 \times 10^{-1}$ |
| 4 | 10% HF, 30 minutes | 30 minutes in running water | 1,100° C., 1 hour, in air | $10\text{-}2 \times 10^{-1}$ |
| 5 | 10% HF, 30 minutes | 30 minutes in running water | 1,250° C., 1 hour, in air | $10\text{-}5 \times 10^{-2}$ |
| 6 | 1% HF, 5 seconds | not conducted | not conducted | $2 \times 10^{-1}$ |

Figure 8:
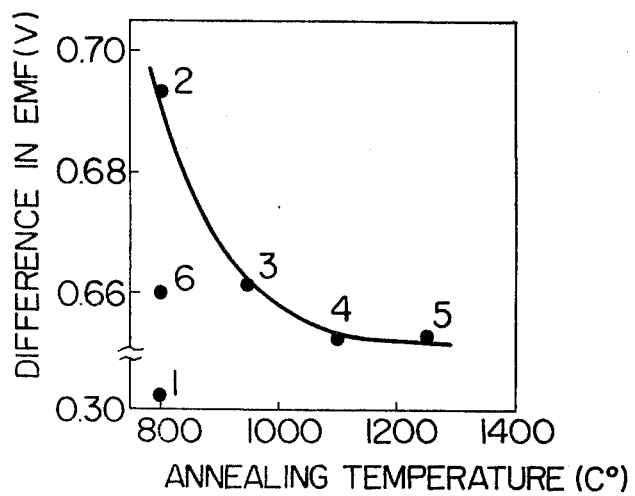
FIG. 8 is a curve illustrating the relation between the temperature at the heat treatment conducted after the treatment with an aqueous solution of HF and the electromotive force characteristic.

Incidentally, numbers 1 to 6 in FIG. 8 correspond to the sample numbers in Table 2.

As will readily be understood from the results shown in Table 2 and FIG. 8, when the heat treatment is conducted at 950° C. or a higher temperature after the HF treatment, the concentration of F left in the surface region of the solid electrolyte is gradually decreased with increase of the heat treatment temperature, and correspondingly, the difference of the electromotive force is gradually diminished. Thus, it is apparent that in order to improve characteristics of an oxygen sensor, it is important that fluorine should be present in the surface region of an oxygen ion conductive solid electrolyte.

EXAMPLE 7

A disc-like sintered body of an oxygen ion conductive solid electrolyte was prepared according to the method described in Example 1. One surface was covered with paraffin and the sintered body was dipped in an aqueous solution of HF. Thus, only one surface of the sintered body was treated with HF.

The paraffin was removed, and electrodes were formed in the same manner as described in Example 1 to prepare an oxygen sensor. Characteristics of the so prepared oxygen sensor were examined. When a gas to be tested ($CO + O_2$) was contacted with the HF-treated surface and the untreated surface was contacted with air, there were obtained results similar to the results shown by curve 12 in FIG. 2. When air was contacted with the HF-treated surface and the gas to be tested was contacted with the untreated surface, there were obtained results similar to the results shown by curve 11 in FIG. 2. Thus, it has been confirmed that when fluorine is contained at least in the surface region on the side contacted with a gas to be tested, an oxygen sensor having excellent characteristics can be obtained.

What is claimed is:

1. An oxygen sensor comprising an oxygen ion conductive solid metal oxide electrolyte having two different surfaces and an electrode formed on each of the two different surfaces of the solid electrolyte, said solid electrolyte comprising means for generating an electromotive force between said two electrodes whereby the oxygen concentration in a gas to be tested is determined from a value of the electromotive force generated between said two electrodes when the gas to be tested is caused to fall in contact with one of said two surfaces of the solid electrolyte and a standard gas having a known oxygen concentration is caused to fall in contact with the other surface of the solid electrolyte, said solid electrolyte containing fluorine at least in the surface region on the side to be contacted with the gas to be tested, the concentration of fluorine in the surface region being between 0.04 and 0.8 weight percent.

2. An oxygen sensor as set forth in claim 1 wherein said solid electrolyte contains fluorine in the surface region on the side to be contacted with the gas to be tested and in the surface region on the side to be contacted with the standard gas.

3. An oxygen sensor as set forth in claim 1 wherein the fluorine-incorporated surface region has a thickness of substantially 50 $\mu$m.

4. An oxygen sensor as set forth in claim 1 wherein fluorine is contained throughout the solid electrolyte.

5. An oxygen sensor as set forth in claim 1 wherein said oxygen ion conductive solid electrolyte is a solid solution of at least one member selected from the group consisting of $ZrO_2$, $HfO_2$, $CeO_2$ and $ThO_2$ with at least one member selected from the group consisting of MgO, CaO, $Y_2O_3$, $La_2O_3$ and $Nd_2O_3$.

6. An oxygen sensor as set forth in claim 1 wherein the gas to be tested is an automobile exhaust gas and the standard gas is air.

* * * * *